US008219433B2

(12) United States Patent  (10) Patent No.: US 8,219,433 B2
Pandya  (45) Date of Patent: Jul. 10, 2012

(54) METHODS FOR ANALYZING JOB FUNCTIONS AND JOB CANDIDATES AND FOR DETERMINING THEIR CO-SUITABILITY

(76) Inventor: Rajiv D. Pandya, Atlanta, GA (US)

(*) Notice: Subject to any disclaimer, the term of this patent is extended or adjusted under 35 U.S.C. 154(b) by 683 days.

(21) Appl. No.: 12/119,228

(22) Filed: May 12, 2008

(65) Prior Publication Data

US 2009/0281879 A1    Nov. 12, 2009

(51) Int. Cl.
    *G06Q 10/00* (2012.01)
(52) U.S. Cl. ..................... 705/7.14; 705/7.21
(58) Field of Classification Search .................. 705/7.14, 705/7.21
    See application file for complete search history.

(56) References Cited

U.S. PATENT DOCUMENTS

| | | | | |
|---|---|---|---|---|
| 5,848,594 A * | 12/1998 | Matheson | ..................... | 600/587 |
| 6,070,143 A * | 5/2000 | Barney et al. | ..................... | 705/8 |
| 6,544,172 B2 * | 4/2003 | Toeppen-Sprigg | ........... | 600/300 |
| 6,735,570 B1 * | 5/2004 | Lacy et al. | ......................... | 705/7 |
| 6,865,581 B1 * | 3/2005 | Cloninger et al. | ................ | 705/9 |
| 7,043,443 B1 * | 5/2006 | Firestone | ........................... | 705/8 |
| 7,818,339 B1 * | 10/2010 | Kay | ............................. | 707/771 |
| 2002/0055866 A1 * | 5/2002 | Dewar | ............................... | 705/8 |
| 2003/0191680 A1 * | 10/2003 | Dewar | ............................... | 705/8 |
| 2004/0122790 A1 * | 6/2004 | Walker et al. | ...................... | 707/1 |
| 2004/0236598 A1 * | 11/2004 | Thomsen | .......................... | 705/1 |
| 2004/0260666 A1 * | 12/2004 | Pestotnik et al. | ................. | 705/2 |
| 2006/0259472 A1 * | 11/2006 | MacClellan | ..................... | 707/3 |
| 2006/0286517 A1 * | 12/2006 | Martin et al. | ................. | 434/219 |

OTHER PUBLICATIONS

Intracorp, "Intracorp Speeds Early Return to Work with New High-Tech Tools," Apr. 11, 2002, PR Newswire.*
Wong, "Toward the Development of a Second Generation Computerized Job-Matching System for Persons with Disabilities: A Conceptual Framework," 1992, Journal of Rehabilitation, Jan./Feb./Mar. 1992 Issue, pp. 70-77.*
Keyserling, "Ergonomic Job Analysis: A Structured Approach for Identifying Risk Factors Associated with Overexertion Injuries and Disorders," May 1991, Appl. Occup. Environ., pp. 353-363.*

* cited by examiner

*Primary Examiner* — Justin M Pats
*Assistant Examiner* — Ivan R Goldberg
(74) *Attorney, Agent, or Firm* — David L King

(57) ABSTRACT

A method and system for conducting an elemental analysis of a job's functions and requirements, conducting a medical diagnosis of a worker to determine the physical capabilities and limitations of the worker, and comparing the elemental analysis and the medical diagnosis to determine whether the worker can function in a particular job be it the current job, another existing job or a modification of either.

4 Claims, 5 Drawing Sheets

| KEY | Weight | Level | Frequency |
|---|---|---|---|
| Abilities Based on Physician Diagnosis | 10 | FW | O |
| Current Job | | | |
| Back Panel and Toe Kick Install | 120 | | |
| | 20 | WS | O |
| | 5 | WS | C |
| Alternative Job in the Worker's Department in the General Order of their Suitability | | | |
| (SB) Buckle Install | 127 | | |
| | 3 | WS | C |
| Back Trim Install | 180 | | |
| | 4 | FW | C |
| | 4 | WS | C |
| Zip Tie | 121 | | |
| | 2 | WS | C |

FOR ASSISTANCE CALL 1-800-937-3219

Physical Demands Options

INTEGRATED HEALTHCARE SERVICES

Company  Location/Project  Job  Search  Reports

Log Out

UnicoreHealth

METHODS FOR ANALYZING JOB FUNCTIONS AND JOB CANDIDATES AND FOR DETERMINING THEIR CO-SUITABILITY

BACKGROUND OF THE INVENTION

1. Technical Field

The technical field of the invention comprises methods and systems for determining whether workers or job candidate are or can be compatible with a particular or any job within a company or group of companies, and vice versa. More specifically, the technical field of the invention comprises a combination of utilities providing for an elemental analysis of a job's functions and requirements, use of the elemental analysis to provide for an employee to return to work after an injury or to provide for specific needs of an employee, use of information regarding a job and injuries reported by employees to create a risk assessment for determining the specific risks of a job at an elemental level, and use of the risk assessment for modifying a job's functions and requirements.

2. Related Art

A major segment of the healthcare industry is comprised of costs associated with workers' compensation, return to work and with determining whether a particular worker is physically or medically suitable for a particular job, and vice versa. Although these include the costs of medical benefits, lost wages benefit payments, premium payments for insurance, and payments made under insurance deductibles, an overarching cost is the time out of work. Another overarching cost is additional time out of work if the worker is re-injured or loses motivation to return to work after returning to work in the previous job, or in a poorly researched substitute job.

Current models of data flow for dealing with worker injuries, return to work, and job placement attempt to link the parties involved in the management of a claim, specifically, the worker (which term includes workers, disabled workers, and job candidates, and other workers, depending on the situation), company supervisor, claims administrator, physician, and ancillary personnel. The mode of transmission is generally via mail, telephone, fax, or, more recently, email. Data is critical for decision-making, which is often sequentially dependent. Problems with the current form of data transmission include the transmission of inaccurate or incomplete information, which may lead to slow and improper disposition of medical care, increased administrative efforts from delays and duplication of tasks, delayed state reporting, bottlenecks in the decision-making process such as delays in authorization of treatments, and a subsequent inability to return the worker to his or her previous job. Often, given the fragmentation of information management, this bottleneck may go unrecognized for periods of time.

Problems with inefficient data flow lead directly to increased expenses including an increase in weekly benefits and administrative costs from delays in returning the worker to work; duplicated tasks, such as inputting or reporting information multiple times; increased administrative and medical costs resulting from repeated or incorrect diagnoses and procedures; fines for delayed state reporting and inappropriate benefit administration; compromised claims management; increased costs due to a decrease in workplace productivity; and increased costs in replacing the worker or in hiring a temporary worker.

One of the largest expenditures in worker's compensation relates to weekly benefits, or "lost time payments" which are generally two-thirds of the workers' salary. A significant cause of extended lost time relates to the employer's lack of available modified duty jobs, and the treating physician's and claims administrator's lack of knowledge of the worker's current job requirements and the alternative positions available to the worker at the employer for his return to a suitable position with his employer. Without such job knowledge physicians will routinely recommend that the worker remain out of work as they generally rely solely on the patient's description of their job duties and assessment of their ability to return to work.

From the employer's perspective, in addition to the hard, quantifiable costs associated with the payment of weekly benefits, the lost time of out-of-work workers results in many soft costs associated with loss of productivity, and those relating to overtime wages paid to co-workers to maintain production schedules, hiring of replacement workers, morale issues for fellow employees, less efficient utilization of skilled workers and a multitude of other potential ramifications, mostly historically non-quantifiable. The worker on the other hand may experience problems related to decreased morale, perceived job insecurity, lower income, and a delay in receipt of other crucial financial benefits due to slow communication.

Often employers will have predetermined modified light duty jobs available for workers. These jobs are sometimes the equivalent of "painting rocks." These are jobs designed to be minimally productive while the worker recuperates, and are often viewed as "punishment" by the worker for being hurt. These "punishment" jobs are not allowed by many states. The only way to truly provide a meaningful modified job is to be able to analyze the physician-imposed restrictions with the worker's current job and all other jobs available at the employer. These problems along with the extended and unwarranted time out of work may lead to increased litigation because the worker feels he is being treated unfairly. In addition, it is historically documented that the longer an worker remains out of work, the less likely they are to return to work as a productive employee of the employer. If the treating physician does not have sufficient information available to determine return to work suitability, often his only recourse is to recommend that the worker remain out of work until the next scheduled appointment.

Central to the management of work-related injuries is the imposition of medical restrictions by a physician. This is to allow healing of the injury without further exacerbation. However, these restrictions often keep the worker from returning to meaningful employment that potentially may be available that does not exacerbate the injury or delay the healing process. This can result from the lack of available modified jobs and/or the treating physician's and claims administrator's lack of knowledge regarding the worker's current job, or possible alternative positions available at the employer. This may lead to increased expenses including lost time resulting in increased weekly benefit payments to the worker; loss of productivity, caused by unskilled replacement workers, poor morale among co-workers, loss of experienced personnel, etcetera; and overtime wages or hiring of replacement employees.

The worker, on the other hand, may experience dissatisfaction with being out of work and, perceive job insecurity and diminished morale. This discontent, compounded by lack of timely medical care and delays in benefit payments, may contribute to an increased desire to pursue litigation. Significant problems by claimants may include: reduction in income; the perception of inadequate medical care; job insecurity; and diminished morale and loyalty to the company over the prospect of his ability to return to work at his employer.

Attempts have been made to address both problems but with only limited success. A comprehensive solution is needed which requires a significant shift in the approach and in the management tools and methods of addressing work related injuries. In order to maximize cost savings to employers, and to provide the most effective medical treatment to workers, a system that provides "real-time" intervention is the ultimate goal.

BRIEF SUMMARY OF THE INVENTION

Briefly, in one embodiment the present invention comprises conducting an elemental analysis of a job's functions and requirements, conducting a medical diagnosis of a worker to determine the physical capabilities and limitations of the worker, and comparing the elemental analysis and/or the medical diagnosis to determine whether the worker can function in a particular job be it the current job, another existing job or a modification of either. In another embodiment the present invention compares the elemental analysis of a database of jobs to the medical diagnosis of an injured worker to determine whether the worker can return to work in a particular job, such as the worker's pre-injury job, or in any job within a company. Thus, in a general embodiment, the present invention can comprise use of the elemental analysis to provide for an employee to return to work after an injury or to provide for specific needs of an employee. Additionally, in another general embodiment, the present invention can use the elemental analysis and the specifics of injuries reported by employees to create a risk assessment for determining the specific risks of a job, and use of the risk assessment for modifying a job's functions and requirements to suit the worker or other workers.

The elemental analysis, in summary, comprises breaking a job down into its component tasks and elements, such as for example but not limited to using the right arm for picking up a widget from the right side, lifting the widget to chest height, moving the widget in front of the body, lowering the widget and placing the widget on a substrate, twisting the widget in place, lifting the widget and substrate to shoulder height, and twisting the torso to the left to place the widget and substrate on a conveyer. The specific job tasks can be further broken down into the various weight requirements of the tasks, such as for example but not limited to lifting a widget weighing no more than five pounds, etcetera, whether the task involves repetitions tasks, and into how the tasks can be accomplished, such as for example but not limited to standing, sitting, extremity position, room temperature, indoors or outdoors, etcetera.

The medical diagnosis, in summary, comprises diagnosing a worker and, for example but not limited to, providing descriptions of the worker's injury and/or condition, providing limitations on physical and/or mental activities, and providing a timeline for recovering from such injury and/or limitations. The physical and/or mental activities can be broken down into specific activities and the limitations attached to such activities. For example, but not limited to, the medical diagnosis can provide that a worker can lift no more than five pounds no more than six times per hour and can only twist the torso no more than 90 degrees. In other words, the medical diagnosis can provide maximum allowable actions in weight and movement.

The comparison between the elemental analysis and the medical diagnosis, in summary, can be initiated by converting the medical diagnosis into maximum allowable actions or restrictions and then comparing the maximum allowable actions or restrictions to the elemental analysis to determine whether the worker's limitations will allow the worker to do the job, whether the job has acceptable task/elemental criteria to accommodate a worker, and whether the task/elemental criteria can be altered to accommodate a worker. More specifically, the medical (or clinical) diagnosis is converted into or saved as restrictions and/or maximum allowable actions and compared to the elemental analysis. Standard medical and clinical criteria are used when creating the restrictions and maximum allowable actions from the medical diagnosis. In other words, the maximum allowable actions link the elemental analysis with the medical diagnosis.

Embodiments of the method and system can be accomplished by a suite of utilities (namely, a suite of steps that preferably are carried out by a computer) that can be carried out individually or in various combinations, or all together, to significantly increase the chance of successfully matching a worker to a job, and vice versa, including determining whether workers or job candidate are or can be compatible with a particular or any job within in a company or group of companies, and vice versa. More specifically, embodiments of the invention comprise a computerized process of steps implementing a suite of utilities providing for an elemental analysis of a job's functions and requirements, comparison of a medical diagnosis of a worker with the elemental analysis, and use of the elemental analysis to provide for an employee to return to work after an injury or to provide for specific needs of an employee, with additional steps including but not limited to use of information regarding a job and injuries reported by employees to create a risk assessment for determining the specific risks of a job, and use of the risk assessment for modifying a job's functions and requirements. Embodiments of the present invention also generally provide for the elemental analysis of a job to allow an employer to determine whether a worker or job candidate is compatible with a particular or any job within in a company or group of companies, and vice versa, in the pre-employment stage, during employment, after a workplace injury, and transferring jobs.

The present invention preferably comprises (a) an elemental analysis utility for creating and using an integrated database of jobs, job functions, job tasks, and job requirements; (b) a medical diagnosis utility for creating and using an integrated database of worker injuries, and of injuries to a particular worker; and (c) a return to work utility for more effectively allowing an injured or disabled worker to return to work and to match job candidates with jobs by comparing the medical diagnosis with the elemental analysis. Additional utilities include (d) a risk assessment utility for parsing the integrated databases to determine the risk of a worker being inured or re-injured when performing a specific job, and (e) a modification utility for allowing the modification of a job to suit a particular worker, preferably based on a comparison of the medical diagnosis with the elemental analysis.

Embodiments of the invention also can comprise a worker diagnosis utility for utilizing a medical or physical diagnosis of a worker or job candidate to match that worker with a particular or any job within a company or group of companies and to using a database of workplace injuries or other worker information to assist in determining the necessary criteria for a job. Further embodiments of the present invention can comprise a utility for allowing company personnel and advisors to contemporaneously communicate to determine whether a particular worker can function in a particular job or in a different job within a company and to increase the ability for a company to retain and place workers in jobs within the company. As a result, embodiments of the present invention can facilitate the development of temporary alternative employment scenarios for workers based on worker injuries or specific needs.

Additional embodiments can include an integrated parsable database comprising information on the company's jobs, the company's workers, injuries to a company's workers, job candidates, required skills, required education, required certifications or credentials, governmental and legal requirements, and combinations of these, is created. This database is parsed according to predetermined criteria based on the utilities disclosed above so as to result in a match between a worker and a job, between a diagnosis and a job, a possibility for adapting a worker or a job to fit the criteria, and/or to assess the risk inherent in a job. As a result, this invention can facilitate return to work after an injury, can decrease lost worker time and productivity by allowing a job to be modified or a worker to return to work in a different, suitable job, and can provide for an elemental analysis of each job task and injuries related to each job task so as to assess the risk of injury of a job or individual job task.

Embodiments of the invention can be used to implement a company-wide method and system for analyzing workers and jobs for determining whether a particular worker is suitable for a particular job, and vice versa, and how a particular worker can alter his or her work mechanics or how a particular job can be made suitable for a particular worker. Although embodiments of the methods and systems of this invention can be used by many different companies, governmental agencies, and universities, both in the manufacturing and service sectors, for ease of this disclosure, the representative embodiments of the invention will be disclosed in conjunction with a single manufacturing company.

These features, and other features and advantages of the present invention will become more apparent to those of ordinary skill in the relevant art upon reading the following detailed description of the preferred embodiments.

BRIEF DESCRIPTION OF THE DRAWINGS

FIG. 4 is a diagnosis based restriction screenshot for entering information about job search parameters on a representative software solution incorporating the present invention.

FIG. 5 is a diagnosis based restriction screenshot for returning information about the results of a job search parameters parsing of the database on a representative software solution incorporating the present invention.

DETAILED DESCRIPTION OF PREFERRED EMBODIMENTS

I. Introduction

Figure 1:
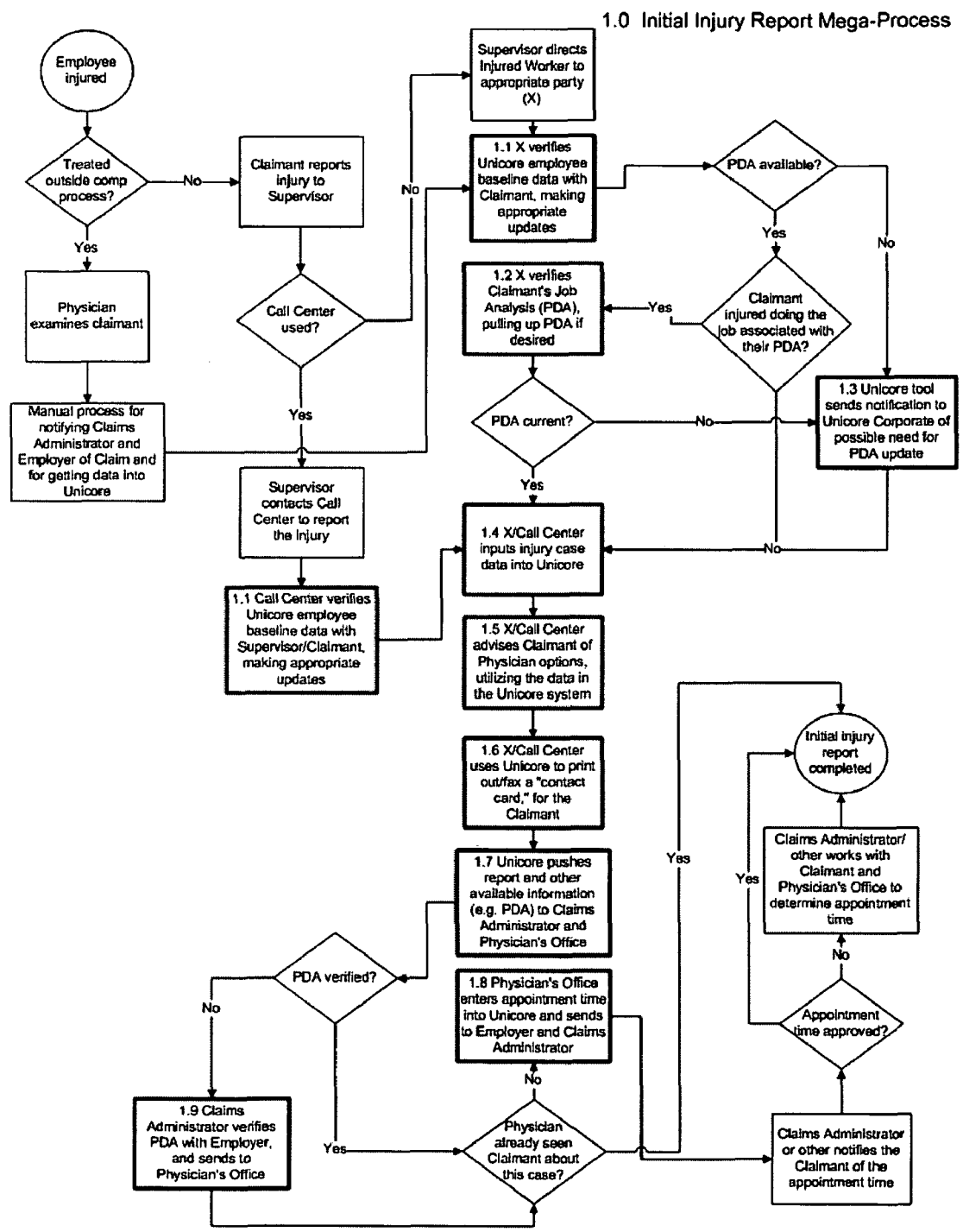
FIG. 1 is a process flowchart of an initial injury report feature of the present invention.

The following detailed description of preferred embodiments is presented only for illustrative and descriptive purposes and is not intended to be exhaustive or limiting. The embodiments are exemplary only and were selected and are described to best explain the principles of the invention and its practical applications. One of ordinary skill in the art will recognize that many variations can be made to the invention disclosed in this specification without departing from the scope and spirit of the invention.

One embodiment of the present invention can comprise conducting an elemental analysis of a job's functions and requirements, conducting a medical diagnosis of a worker to determine the physical limitations or physical abilities the worker is capable of, and comparing the elemental analysis and the medical diagnosis to determine whether the worker can function in a particular job. For example, a job can be divided up into individual tasks, with each task being broken down into elemental parts. Such elemental parts can be objectively described by the physical and/or mental functions associated with each task, such as for example physical movements, weights, and repetitions involved. These elemental parts can be collected into an integrated parsable database and computerized for ease and speed of searching and comparing. In this same example, a worker can undergo a medical diagnosis (a medical check-up) to determine what the worker is capable of. For example, in conducting a medical diagnosis of an injured worker, a doctor can recommend that the worker limit his activities and actions to certain maximum allowable units, such as maximum weight lifted, maximum repetitions per hour, maximum time standing or sitting, and maximum body motions such as twisting or bending. These maximum allowables also can be collected into an integrated parsable database and computerized for ease and speed of searching and comparing. The maximum allowables determined in the medical diagnosis that can be compared to the elemental analysis to determine a fit between a worker and a job.

Another embodiment of the present invention can compare the elemental analysis of a database of jobs to the medical diagnosis of an injured worker to determine whether the worker can return to work in a particular job, such as the worker's pre-injury job, or in any job within a company or work location. In this embodiment, the maximum allowables resulting from the medical diagnosis initially can be compared with the elemental analysis of the worker's original job to determine whether the worker can return to work at her original job. If not, the worker's maximum allowables can be compared to the elemental analyses of a portion or of all of the jobs within a company, family of companies, or group of companies to determine whether the worker can return to work in any job within the company, family of companies, or group of companies.

A further more general embodiment of the present invention can comprise use of the elemental analysis to provide for specific needs of an employee. In this embodiment, the maximum allowables can be compared to the elemental analyses of various jobs and if no appropriate jobs are available, or if a desired job is not appropriate, the elemental analyses can be reviewed to determine if the job can be altered to accommodate the worker.

Additionally, another general embodiment of the present invention can comprise use of the elemental analysis and the specifics of injuries reported by employees to create a clinically relevant risk assessment for determining the specific risks of a job, and use of the risk assessment for modifying a job's functions and requirements to suit the worker or other workers. For example, the various injuries occurring in connection with a specific job can be tagged to the elemental analysis. The various injuries can be assessed using standard statistical techniques to result in a determination of the likelihood of such injuries occurring in the future by workers on this job.

The elemental analysis, in summary, comprises breaking a job down into its component tasks. Component tasks can include, for example but not limited to, tasks such as using the right arm for picking up a widget from the right side, lifting the widget to chest height, moving the widget to in front of the body, lowering the widget and placing the widget on a substrate, twisting the widget in place, lifting the widget and substrate to shoulder height, and twisting the torso to the left to place the widget and substrate on a conveyer. The specific job tasks also can be further broken down into the various weight requirements of the tasks. Weight requirements can include, for example but not limited to, lifting a widget weighing no more than five pounds, sliding a part weighing no more than ten pounds, and pulling a lever with no more than seven pounds of force. Additionally, the specific job tasks also can be further broken down into whether the task involves repetitions tasks, and into how the tasks can be accomplished, such as for example but not limited to standing, sitting, room temperature, indoors or outdoors, etcetera. The elemental task information is entered into a database, preferably a parsable database, and more preferably a computerized parsable database.

The medical diagnosis, in summary, comprises diagnosing a worker. A typical medical or clinical diagnosis can include, for example but not limited to, providing descriptions of the worker's injury, providing limitations on physical and/or mental activities, and providing a timeline for recovering from such injury and limitations. The physical and/or mental activities can be broken down into specific activities and the limitations attached to such activities. For example, but not limited to, the medical diagnosis can provide that a worker can lift no more than five pounds no more than six times per hour and can only twist the torso no more than 90 degrees. In other words, the medical diagnosis can provide maximum allowable actions in weight and movement. The maximum allowables can be entered into the same database as the elemental analysis, but preferably either is entered into a separate database or is maintained as separate data pertaining to a particular worker. For example, while the elemental analysis data can be pertinent to all medical diagnoses and therefore preferably should be parsable relative to all workers, the medical diagnoses can be and generally are specific to each individual worker.

The comparison between the elemental analysis and the medical diagnosis, in summary, can be initiated after converting the medical diagnosis into the maximum allowables and then comparing the maximum allowables to the elemental analysis to determine whether the worker's limitations will allow the worker to do the job, whether the job has acceptable task criteria to accommodate a worker, and whether the task criteria can be altered to accommodate a worker. Standard medical and clinical criteria are used when creating the restrictions and maximum allowable actions from the medical diagnosis. In other words, the maximum allowable actions link the elemental analysis with the medical diagnosis.

The present invention comprises several utilities that can be carried out individually or in various combinations, or all together, to increase the chance of successfully determining whether a worker, such as an injured worker, can return to a previous job, or more generally matching a worker to a job, and vice versa. The present invention preferably comprises (a) an elemental analysis utility for creating and using an integrated database of jobs, job functions, job tasks, and job requirements; (b) a medical diagnosis utility for creating and using an integrated database of worker injuries, and of injuries to a particular worker; and (c) a return to work utility for more effectively allowing an injured or disabled worker to return to work and to match job candidates with jobs by comparing the medical diagnosis with the elemental analysis. Additional can utilities include (d) a risk assessment utility for parsing the integrated databases to determine the risk of a worker being inured or re-injured when performing a specific job, and (e) a modification utility for allowing the modification of a job to suit a particular worker, preferably based on a comparison of the medical diagnosis with the elemental analysis.

Each utility can have the ability to query the elemental analysis database to provide information relevant to the utility so as to be able, for example (a) to pair a worker with the most suitable job or a job with the most suitable worker, (b) to allow the adaptation of a job to a worker or to address recurring workplace injuries resulting from the job, (c) to allow the modification of a worker's tasks in performing a job to address an injury or recurring workplace injuries resulting from the job, (d) to determine whether a job candidate is suitable for a particular or any job and vice versa, (e) to use a medical or physical diagnosis of a worker to determine whether a job is available for the worker or whether a job can be adapted to such a worker, and (f) to assess the risk of future workplace injuries resulting from a job.

Throughout this specification, various terms will be used in a general sense and are meant to encompass or include a range of subsets. The term worker includes workers, disabled workers, injured workers, and job candidates, depending on the situation. The term company includes all types of companies, universities, governments and government agencies, partnerships, and proprietorships, and further includes all of the company's internal and external administrators such as but not limited to human resource professionals and medical professionals. The term job includes all jobs, professional, paraprofessional, vocational, skilled or unskilled. The terms tasks or elements include the various specific activities and actions that make up a job. Although the methods and systems of this invention can be used by many different companies, governmental agencies, and universities, both in the manufacturing and service sectors, for ease of this disclosure, the invention will be disclosed in conjunction with a single manufacturing company.

II. General Features

The invention can be used to implement a company-wide, work location-specific method and system for analyzing workers and jobs for determining, for example, whether an inured worker can return to the worker's job, whether a particular worker is suitable for a particular job, and vice versa, and how a particular worker can alter his or her work mechanics or how a particular job can be adapted to a particular worker. In short, an integrated parsable database comprising elemental analysis information on the company's jobs, the company's workers, injuries to a company's workers, job candidates, required skills, required education, required certifications or credentials, governmental and legal requirements, and combinations of these, is created. This database is parsed according to predetermined search criteria based on the utilities disclosed above so as to result in a match between a worker and a job, between a diagnosis and a job, a possibility for adapting a worker or a job to fit the criteria, and/or to assess the risk inherent in a job.

A feature of the invention is the creation of a standard, objective parsable database of at least the requirements for specific jobs within a specific company. Additional information can be included in the database such as, but not limited to, on-the-job injuries to workers and how these injuries occurred, and governmental and other regulations and requirements for workers and jobs. Another feature of the invention is a means for parsing the database so as to allow the comparison of a worker to a job, and vice versa, so as to determine the co-suitability of the worker to the job, and vice versa. This parsing function allows the user, such as the company, to determine the best job for a worker, whether a job can be adapted to a worker, and the risks associated with a job relative to a worker. In a simple form, the present invention can provide the company, as well as physicians, other health practitioners, human resource persons, and risk management persons, the knowledge of the tasks, elements of tasks and qualifications required of specific jobs within a company, thus allowing a more objective determination of whether a person is suitable for a job, such as whether a potential employee is capable of performing a specific job, whether a job can be modified for a potential or existing employee, and/or whether an employee can return to work, either in the original job or, if not, in another job within the company or in related or other companies.

The database can be created in many ways by inputting the desired information. For example, a task-specific job analysis can be conducted of the physical requirements for each job. For another example, a physical demands analysis can be completed giving a written and/or a pictorial description of the various functions involved in carrying out the job. In the job analysis and physical demands analysis, the various restrictions and maximum allowable physical requirements of a worker, through the medical diagnosis, is compared with the restrictions or maximum allowable actions and requirements of each specific task of a job, can be quantified and included in the database. In other words, an elemental analysis of each job is conducted and the elemental restrictions and requirements are included in the database. Then the database can be parsed in connection with the various utilities of the invention.

Additionally, government regulations and rules can be inputted and cross-referenced to specific jobs; educational, certification, and credentialing analyses can be completed for each job; and workplace injuries, how the injuries occurred, and what effect the injuries had on the worker can be compiled. All of this information can be inputted into the database, cross-referenced, and made available in a parsable format by one of ordinary skill in the database creation field. By parsing this type of database, the suitability of a worker for a job or a job for a worker, the risk assessment of a job or a job task, and the ergonomics of a job can be determined for an injured worker in a return to work situation or for the hiring of a new worker.

In an alternative embodiment, the present invention can help companies and workers find suitable matches between the worker and the company's job bank. Use of the parsable database can find alternative jobs that a worker can do. For example, in use, the database can be parsed by maximum weight the employee is able to lift, maximum frequencies of motion or movement an employee is able to do, and/or the physical activities the employee is able to do. Similarly, the database can be parsed in the employment process by allowing the employee to input his or her physical limitations and jobs that the company has available then will be returned, and the worker and the company can decide if the worker is right for the job. This is advantageous in both the return to work and hiring processes.

In another alternative embodiment, the present invention can help companies use medical and physical diagnoses of workers to find suitable jobs for workers and to adapt current jobs to particular workers or a particular workforce. For an example in use, a medical diagnosis, which could include tasks the worker can and cannot perform, can be compared with the company's jobs. Jobs that the company has available that satisfy the diagnosis criteria then will be returned, and the worker and the company can decide if the worker is right for the job. This also is advantageous in both the return to work and hiring processes.

In another alternative embodiment, the present invention can help companies use worker injury data to adapt jobs and to assess the risk of future injuries by workers carrying out jobs. When injury data is cross-referenced to jobs, it can more easily be determined whether a job has a higher risk of injury, and what that injury might be. Additionally, this injury information can be used to adapt the job so as to possibly reduce or eliminate the risk in the future. This is advantageous in the return to work and jibe creation and adaptation processes.

A. Elemental Analysis Utility.

As already disclosed, job elemental analysis includes breaking a job down into elemental tasks and the physical and mental requirements of each task. A database of the jobs and elemental tasks is created for parsing in other utilities.

B. Medical or Clinical Diagnosis.

As already disclosed, diagnosis includes using a medical or physical diagnosis of a worker to determine the suitability of a worker for the worker's original job, a different existing job, the same job but altered in some form, or a different existing job but altered in some form, or whether a job candidate can satisfy the criteria for existing jobs or for existing jobs altered in some form. For example, the post-injury worker may have different physical abilities than the pre-injury worker, and one worker may have different physical abilities and needs than another worker. The medical or physical diagnosis utility can be used to determine whether a worker can return to work in the same job, a different existing job, the same job but altered in some form, or a different existing job but altered in some form, or whether a job candidate can satisfy the criteria for existing jobs or for existing jobs altered in some form. This utility can include:

(1) Utilizing a medical or physical diagnosis that leads to restriction of a worker to match that worker with a particular or any job within a company;

(2) Utilizing a medical or physical diagnosis of a person to determine the restrictions for a worker to take a job, based on the maximum allowable tasks for the job;

(3) Utilizing this diagnosis-based assessment of a person to translate the restrictions for a worker into the maximum allowable tasks for the worker so as to be able to match the worker to a job and vice versa;

(4) Allowing searching of the database for a listing of possibly appropriate jobs for the worker, determining why or why not a job can or cannot be done by the worker, and then matching the restrictions with all job elements in a company; and/or (5) Applying the diagnosis-based assessment to qualifications or essential functions required by, for example, the Americans with Disabilities Act so as to allow searching of the database for a listing of possibly appropriate jobs for the worker.

In a simple working example, the medical diagnosis can operate as follows. The doctor sees patient, namely, the worker. The doctor, based on the injury, makes a diagnosis of the worker. As part of this diagnosis, the doctor further makes recommendations regarding the worker's ability to handle certain tasks. For example, as already disclosed, the recommendations may include that the worker cannot do certain tasks at all for two weeks, that the worker cannot lift more than five pounds, that the worker cannot twist more than 90 degrees, that the worker can perform no more than seven repetitions per minute, etcetera. The doctor then prescribes these restrictions as the maximum allowables. Alternatively, the system, based on historical data, can use known artificial intelligence methods to prescribe restrictions.

C. Return to Work Utility.

This utility can be defined as determining whether a worker can return to work in the same job, a different existing job, the same job but altered in some form, or a different existing job but altered in some form. The medical diagnosis for a particular worker can be used to parse the elemental analysis database for making this determination. Similarly, this utility can be used in the hiring of new employees. That is, a new worker's physical and educational skills and training can be used to determine whether the new worker satisfies the criteria for existing jobs or for existing jobs altered in some form. The return to work utility can be used in determining whether a worker can return to work in the same job, a different existing job, the same job but altered in some form, or a different existing job but altered in some form. This utility can include:

(1) More effectively allowing a worker to return to work in a particular job or any job within a company;

(2) Allowing personnel and advisors to contemporaneously communicate to determine whether a particular worker can function in a particular job or in a different job within a company;

(3) More effectively getting a disabled worker back to work;

(4) Determining whether a worker has the appropriate faculties for a specific job or for any job in the database both during the pre-employment process and post injury; and/or (5) Allowing a ranking of jobs suitable for the physical capabilities of a worker and basing the ranking on jobs with the most suitable elements and/or jobs within or proximal to the worker's pre-injury job or team, pod, group, division, etcetera. The graphic representation of this ranking as shown in FIG. 5 accomplishes another important objective in that it translates the clinical terms used by the physician into the terms of the specific tasks and elements used by the employer.

This utility also can comprise a hiring utility that can be used in determining whether a worker's physical and educational skills and training satisfy the criteria for existing jobs or for existing jobs altered in some form. This utility can include:

(1) Determining whether a worker has the abilities and faculties necessary for a particular or any job within a company;

(2) Determining whether a particular job within a company is suitable for a particular or any worker;

(3) Increasing the ability for a company to retain and place workers in jobs within the company;

(4) Creating and using a database listing maximum allowable tasks for jobs, including searching the database to find a job suitable for an individual;

(5) Determining whether a worker has the appropriate faculties for a specific job or for any job in the database both during the pre-employment process and post injury;

(6) Allow a ranking of jobs suitable for the physical capabilities of a worker and basing the ranking on jobs with the most suitable elements and/or jobs within or proximal to the worker's pre-injury job or team, pod, group, division, etcetera; and/or (7) Allowing a matching of a worker's certifications, training, and/or credentialing with the jobs in a database.

D. Risk Assessment Utility.

This utility can be used to determine what elements of a job are more prone to causing injuries and to adapting jobs or job elements to compensate or reduce such risks. Similar to a job elemental analysis, an elemental risk assessment can be made of each job by taking past injuries that occurred for the job and creating a database of such injuries. The risk assessment utility can be used to parse a database of past injuries to determine what elements of a job are more prone to causing injuries and to adapting jobs or job elements to compensate or reduce such risks. This utility can include:

(1) Utilizing a physical demands analysis (elemental analysis) and scalability to create and use a database to help show which task of a job is associated with a specific risk of injury;

(2) Allowing a comparison of job elements for creating a risk assessment of whether a specific job or a specific task will or does have a higher risk of causing injury to a worker or causing a repeat injury to a previously worker; and/or (3) Allowing the creation of risk management reports based on job tasks.

E. Modification Utility.

This utility can be used to create and modify jobs based on worker abilities, skills, and training. For example, the worker diagnosis and the risk assessment can be used to create the criteria, tasks, and elements for new jobs or to adapt the criteria, tasks, and elements of existing jobs to more fully employ workers. The job creation and adaptation utility allows the use of worker abilities, skills, and training to create the criteria, tasks, and elements for new jobs or to adapt the criteria, tasks, and elements of existing jobs to more fully employ workers. This utility can include:

(1) Using a database of workplace injuries or other worker information to assist in determining the necessary criteria for a job;

(2) Allowing a searching of jobs at other related companies to allow workers at one related company to be transferred to other related companies, or to allow workers at one governmental agency to be transferred to other governmental agencies; and/or (3) Allowing a categorization of the jobs based on various hierarchies, such as department, facility, physical requirements, essential or non-essential functions, etcetera.

III. Database

The database can include information about jobs, workers, injuries, regulations, etcetera. Generally, the database preferably comprises the elemental tasks of each job and allows a parsing of the database based on criteria for allowing a worker to perform the tasks of a job. In this manner, workers can be matched to jobs that the workers can physically handle. Specifically, the innovation of creating the database, matching the database up with clinical data of physical restrictions and requirements, and applying the database to workers to determine worker suitability for a specific job is a preferred feature of this invention. The innovation of breaking a job down into workstation, tasks and elements, matching up injury data with each workstation, task and element, and determining whether an individual workstation, task or element is more likely to cause an injury or whether an injury is more likely to occur when performing an individual workstation, task or element is another feature of this invention.

Jobs are analyzed in terms of elements and tasks. An element is the smallest step into which it is practical to subdivide any work activity without analyzing separate motions, movements and mental processes involved. A task is one or more elements and is one of the distinct activities that constitute logical and necessary steps in the performance of work by the worker. Further, jobs may be broken down in terms of positions. A position is a collection of tasks constituting the total work assignment of a single worker. Finally, a job is a group of positions within an employment setting, which are identical with respect to their major or significant tasks and sufficiently alike to justify their being covered by a single analysis.

Each element is analyzed in terms of its physical demands. Strength requirements are obtained using standard job analysis equipment. Definitions for physical requirements are taken from, for example, commonly available sources such as *The Revised Handbook for Analyzing Jobs* published by the United States Department of Labor, Employment and Training Administration in 1991. For example, work can be categorized as sedentary work, light work, medium work, heavy work, and very heavy work. Elements can include such activities as standing, walking, sitting, lifting, carrying, pushing, pulling, climbing, balancing, stooping, kneeling, crouching, crawling, and reaching.

Essential functions are any element of the task that must be completed by the worker without assistance and without modification. If a worker is unable to perform an essential function he is unable to complete his required job duties. Thus, for example, when creating the job portion of the database, one must take into account whether removing the function fundamentally changes the job, if the function is critical to overall performance of the job, if an assistant can be used to assist the worker in the function, as well as other questions.

The parsable database is created to allow for more effective return to work and retention of jobs. By breaking a job down into workstations, specific tasks, and inputting this elemental analysis (for example, physical job restrictions and requirements) into the parsable database, a job can be matched up a worker according to essential and non-essential functions as determined by the employer and weighted by the employer. Similarly, a medical professional can provide clinical restrictions (maximum allowables) for a job (for example, physical restrictions based on a hypothetical ordinary or average worker could or should be able to accomplish), which can be inputted into the parsable database. In this manner, the various restrictions and requirements of a job are available for parsing and matching to a worker.

IV. Parsing

The present invention has been specifically and uniquely designed to address and expedite early and appropriate return to work options. The primary component of this system is a parsable database that allows the user to view specific tasks associated with each job, including all physical demands of the job. The invention can graphically show (1) a list of the specific elements of the worker's job that fall inside and outside of the parameters of the restrictions, (2) a list of other jobs available with the employer that are within the restrictions or are closest to the restrictions, and (3) specific injuries that occur during individual job tasks. By identifying the specific elements with their physical requirements, the user can isolate the elements that the worker is unable to perform and assist in identifying alternative jobs, tasks or methods that are within the imposed physical restrictions, and create a risk assessment for a particular job or job task. The graphic representation of this ranking as shown in FIG. 5 accomplishes another important objective in that it translates the clinical terms used by the physician into the terms of the specific tasks and elements used by the employer.

The present invention enables the company to evaluate return-to-work issues from the beginning of care. Using the present invention, the company is able to make a more accurate disposition of the worker's case, hopefully resulting in an early and safe return to work in the same job, the same job adapted based on the injury or diagnosis, a different job, or a different adapted job. Further, the company can utilize the search engine to determine if there are any other jobs at the facility or company-wide that the worker can currently perform within the restrictions set out by the physician or in the medical diagnosis. This allows a determination to be made to see if these tasks can be reasonably modified to allow the worker to return to his original, albeit, modified position.

As a first illustrative example of how the present invention operates, assume a worker at an auto assembly plant injures his back while lifting a heavy component. The worker reports the injury to his supervisor who communications the situation according to established policy. During the initial medical examination the physician can use the information contained in the database about the worker's job as an aid in determining medical restrictions for the worker.

When examining the worker and developing a medical diagnosis, the physician can view still photos, video and metrics regarding the worker's job and thus more accurately determine the amount of weight the worker can carry, or the length of time standing is permitted, or other such work restrictions or allowable actions. The present invention will compare these restrictions with the information worker's job and other jobs in the database, and the system will provide a listing of jobs in descending order of jobs (if any) that satisfy the physician's criteria, to jobs that satisfy most of the physician's criteria, to jobs that satisfy only some of the physician's criteria, and so on. The company is now able to make a reasonable recommendation for the worker's ability to perform the worker's job and, if not, whether there are other jobs in the company that the worker can do in the injured and recovered state. Alternatively, the company can review the listing of jobs and determine whether any of the jobs can be modified to accommodate the worker. If desired, the company can even search other jobs at other company locations to locate one that may be easier to modify to comply with the restrictions.

Contemporaneously, the injury data is attached in the database to the specific job and job task during which the injury occurred. As the injury data is compiled, that is when additional injury data is inputted into the database, an injury profile is created for a specific job and job task. Using this data, a risk assessment for the job and job task can be created, and the occurrence of a future injury can be predicted. Additionally, the injury data can be used to modify the job. Thus, the database can be parsed both for determining whether a current job and job task has a risk of injury or a high predictability of an injury occurring, and for jobs and job tasks that could or should be modify to reduce the risk of future injury. Thus, the present invention provides a clinical model of the risk of injury due to a job or job task, what the injury is likely to be, and why the injury occurred.

A parsing of the database can generate a listing of the types of injuries occurring and the frequency of the injuries in elemental detail, that is, which job element is prone to injury. Thus, the job element can be modified (e.g., lowering a maximum lifting weight), or a different worker or assistant can be assigned to the job (e.g., a stronger worker to carry out the specific task), or in the case of return to work assigning the injured worker to a different job. Thus, a risk prediction database can be developed for each job task, each job, or each company. This results in a very powerful tool for predicting risk based on job tasks, namely, the ability to identify which workers with particular medical diagnoses can or cannot perform a job or a job task. If the job task is an essential element of the job, the diagnosed worker can be assigned to a different job, the job can be modified, or an assistant can be assigned to carry out the job task.

One aspect of the parsing ability is predicting risk based on previously reported and inputted job injuries. The present invention comprises a very powerful tool for predicting injury risk because each injury is attached to a specific job task and therefore the injury risk assessment is based on elemental analysis. The database can be parsed for a particular type of restriction or a particular type of injury and, based on the injury, the invention can identify jobs for workers who have medical restrictions either from previous lifting injuries or a medical diagnosis. With the present invention, a company can parse workers with a particular diagnosis and break down how many elemental (or job task) injuries occurred and what the elemental injuries were, and use the job elemental analysis to determine and evaluate worker risk relative to a job or job task. In other words, the present invention matches a job elemental analysis with a worker diagnosis to allow the company to determine whether the worker is suitable for the job and vice versa. Comparing a job at the elemental analysis level with a worker medical diagnosis can allow the company to determine which jobs or job task is an injury risk. Thus, by capturing a medical diagnosis (injury) associated with a particular job task element and capturing that data, a company is able to determine or predict, based on particular job task elements and historical injuries throughout the entire company, the risk of injury.

V. Illustrative Embodiment

Referring now to the figures, an illustrative embodiment of various features of the invention is disclosed. Some of the figures are flowcharts illustrating the information gathered for input into the parsable database and how the database can be used to carry out the various utilities of the invention. Some of the figures are screen shots of a software application developed for carrying out the invention illustrating the information that can be parsed in the database and typical results that are returned. Overall, a disclosure of how the inventive database is created, updated, and used is provided by these figures and the connected disclosure.

FIG. 1 is a process flowchart of an initial injury report feature of the present invention. As can be seen, this flowchart initiates upon an injury to an employee (worker) and terminates upon the completion of the initial injury report. After an employee is injured, various actions are triggered including reporting the injury to the supervisor and a medical examination of the employee by a physician. Both the supervisor's report and the physician's report can be inputted into the database. For example, among other permutations, the injuries received can be inputted into the database as a function of the job or job task that was being carried out when the injury occurred. In this manner, the job portion of the database can be updated with the information about potential injuries that can occur related to the job or job task. Similarly, the injuries can be inputted into the database as a function of the worker. In this manner, the worker portion of the database can be updated with the information about injuries specific workers have received.

Figure 2:
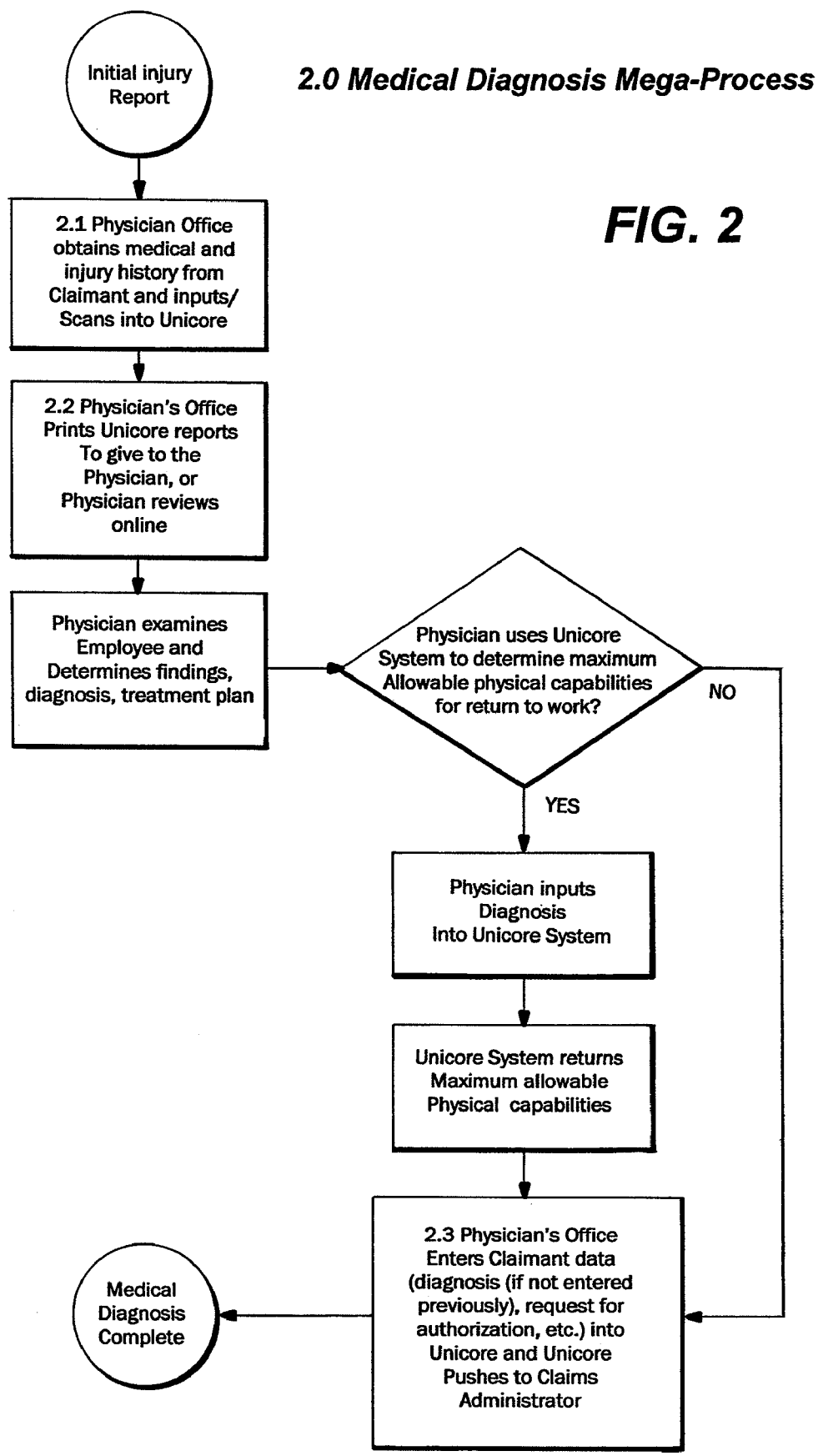
FIG. 2 is a process flowchart of a medical diagnosis feature of the present invention.

FIG. 2 is a process flowchart of a medical diagnosis feature of the present invention. As can be seen, this flowchart initiates upon the completion of the initial injury report and terminates upon the completion of the medical diagnosis. After the initial injury report is completed, the physician, for example, can access the database for other information about the worker, which may be helpful in diagnosing and treating the worker. The physician then can conduct an examination of the injured worker and can determine a diagnosis and treatment plan. The physician can input this information into the database, including information about the worker's physical capabilities and the maximum allowables. The database then can be parsed to determine whether the worker, based on the medical diagnosis and the worker's maximum allowable physical capabilities as a result of the injury, can return to work in the original job, in a substitute job, or not at all. All of this information comprises the completed medical diagnosis.

Figure 3:
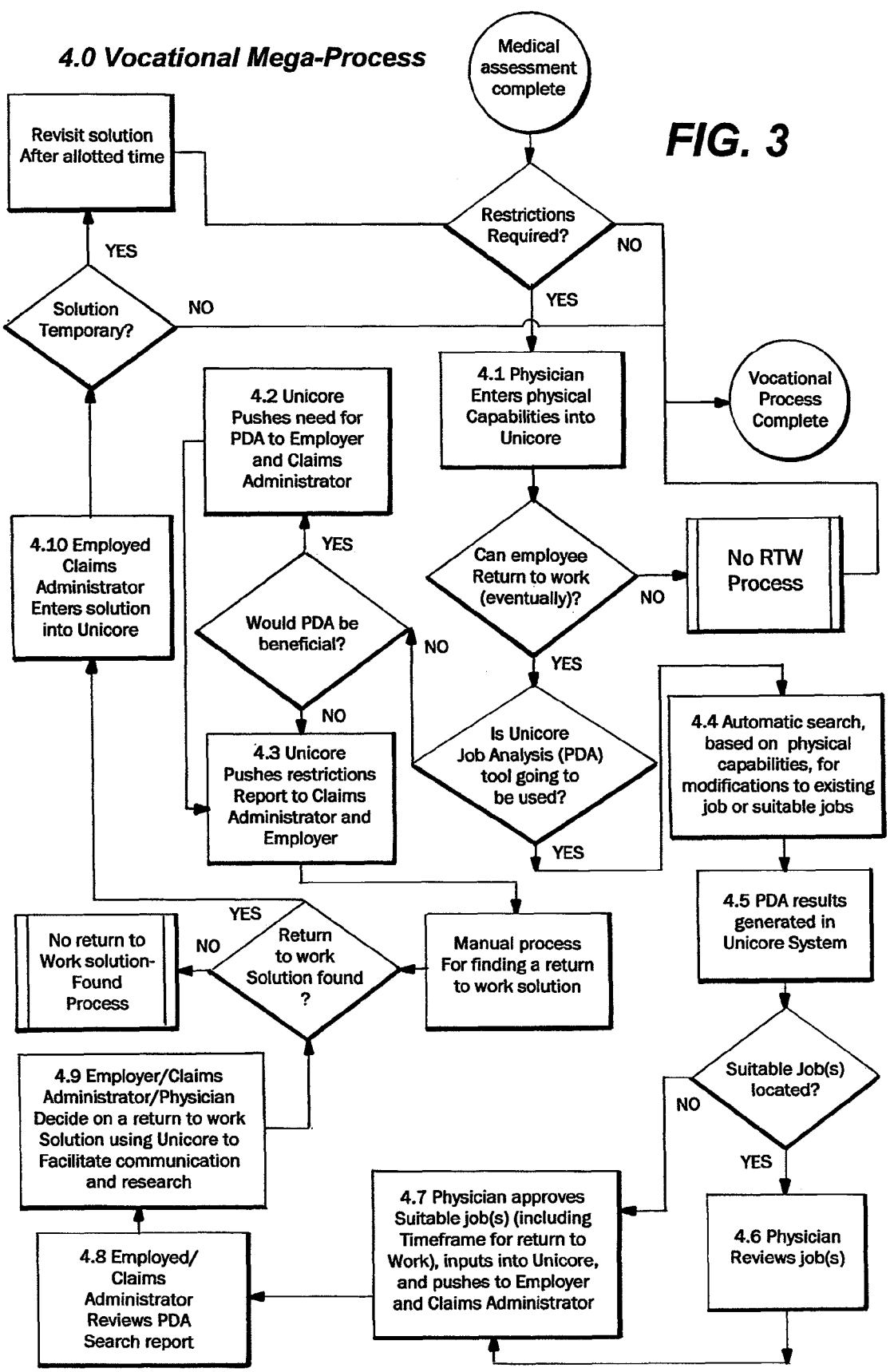
FIG. 3 is a process flowchart of a vocational feature of the present invention.

FIG. 3 is a process flowchart of a vocational feature of the present invention. As can be seen, this flowchart initiates upon completion of the medical diagnosis and terminates upon the completion of the vocational process. After the medical diagnosis is completed, the physician can enter the worker's physical capabilities into the database, including a diagnosis as to whether the worker can return to work in the same job, the same job after a period of recovery, a different job, or not at all. This process can be used to find alternative jobs or for modifying original jobs for workers that have been injured but not seriously enough to prevent a return to work. By entering the restrictions into a search feature of the database (see FIG. 4, for example), the database can be parsed based on the physical capabilities of the worker and a listing of jobs returned (see FIG. 5, for example) that may be appropriate as is or somewhat modified for the worker. The physician and the company then can review the resulting list of jobs and determine whether any one or more of those jobs can be carried out by the worker.

Additionally, after parsing the database, if no appropriate job is returned (see FIGS. 4 and 5 and the connected disclosure), then one option would be to change the medical treatment of the worker to allow the worker to be able to perform a different job. Using the alternative jobs obtained from the database as a starting point, the physician can revise the worker's treatment plan to allow the worker to perform the alternative job. This new information can be inputted into the database for use in later situations, such as if a similar situation occurs, and the alternative job and treatment plan can be returned in the results of parsing the database.

The information gleaned and created during each of the above processes can be used by other utilities in determining whether the worker can return to work in the same job, a different job (for example, a different job in the company having physical maximums in line with the medical diagnosis), or not at all, as disclosed herein. This information also can be used by the physician and/or the company in prescribing whether a particular worker can carry out a particular job or job task, or in modifying a particular job or job task, in that a particular worker may no longer be able to carry out the job or a job task based on the medical diagnosis of the injury. Similarly, this information can be parsed when determining whether a particular job can be carried out by a particular worker (for example, by parsing the database for jobs that have physical maximums in line with the medical diagnosis) and in determining the risk of injury assessment of a particular job or job task, for current workers, inured workers, or new hires.

Figure 4:
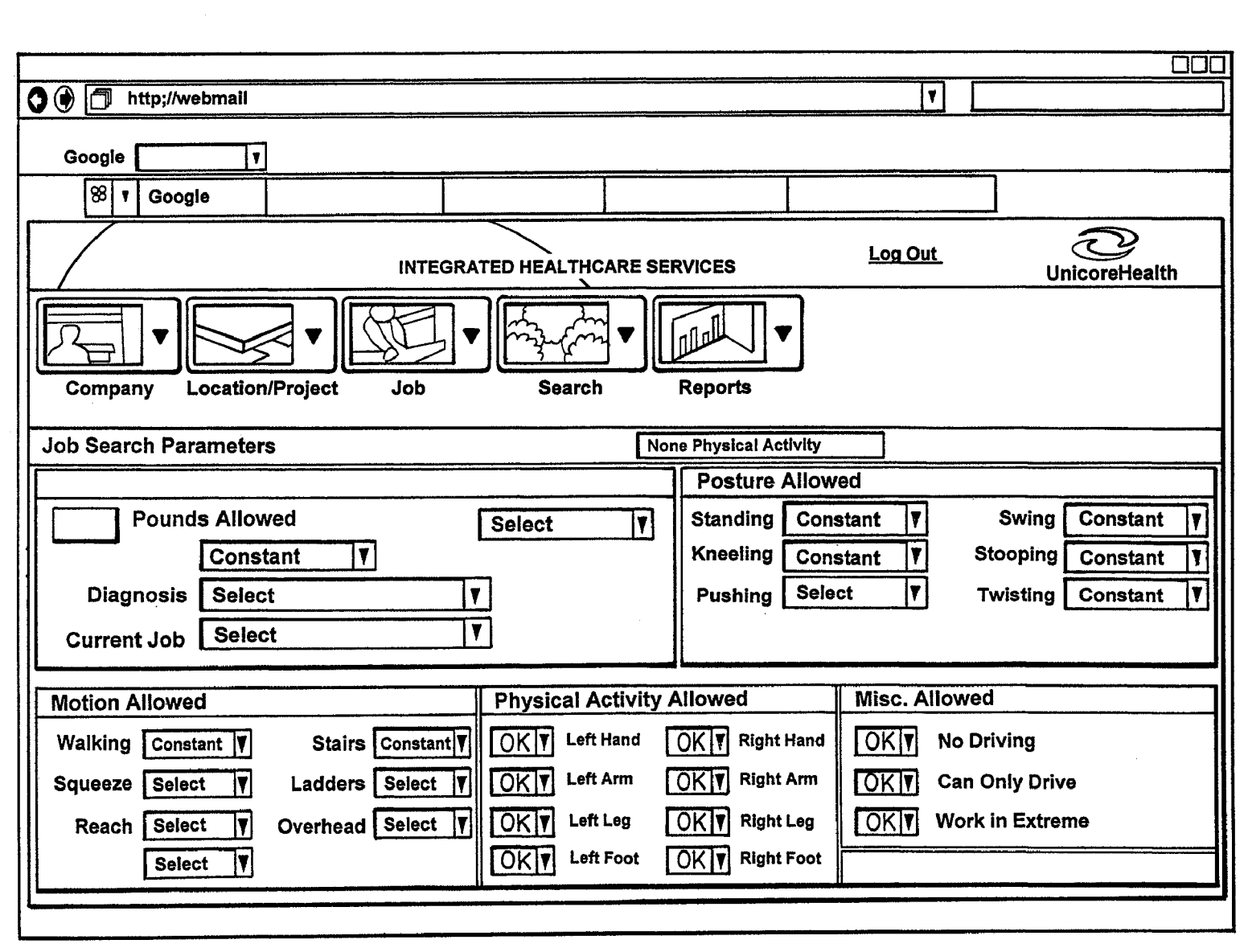

FIG. 4 is a diagnosis based restriction screenshot for entering information about job search parameters on a representative software solution incorporating the present invention. This is an input page in which various job search parameters are entered for parsing the database. For example, maximum weight lifting or motion criteria can be entered based on the medical diagnosis, and the database will be searched using these criteria. As in conventional database parsing, one or more criteria can be searched, with the more criteria searched the more likely an appropriate job will appear on the results screen (FIG. 5). Thus, such a search parameter input interface can be used to parse the database for obtaining results for each of the utilities and processes disclosed herein.

FIG. 5 is a diagnosis based restriction screenshot for returning information about the results of a job search parameters parsing of the database on a representative software solution incorporating the present invention. This is an output page in which various possibly appropriate jobs are presented for consideration based on the input criteria (FIG. 4). For example, the current job parameters are displayed (the job that the worker was performing pre-injury) as well as alternative jobs based on the search criteria. The various physical restrictions (parameters) are displayed, some of which may satisfy the searched criteria and some of which may not. If a job is returned that satisfies all of the search criteria, this job likely is appropriate for a return to work. Other jobs also can be returned that may not satisfy all of the search criteria, but which may be modifiable so as to be appropriate for a return to work.

Thus it can be seen that the inventive database, utilities, and processes allow for a constant and continuous updating of a parsable database of criteria that are useful for various situations in determining whether a job is appropriate for a worker and vice versa. This integrated parsable database comprises information on the company's jobs, the company's workers, injuries to a company's workers, job candidates, required skills, required education, required certifications or credentials, governmental and legal requirements, and combinations of these. This database can be parsed according to predetermined criteria based on the utilities disclosed above so as to result in a match between a worker and a job, between a diagnosis and a job, a possibility for adapting a worker or a job to fit the criteria, and/or to assess the risk inherent in a job. As a result, this invention can facilitate return to work after an injury, can decrease lost worker time and productivity by allowing a job to be modified or a worker to return to work in a different, suitable job, and can provide for an elemental analysis of each job task and injuries related to each job task so as to assess the risk of injury of a job or individual job task.

The foregoing detailed description of the preferred embodiments have been presented only for illustrative and descriptive purposes and are not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

What is claimed is:

1. A method for determining whether an injured worker can return to work in their current job, a different existing job, the current job but altered in some form, or a different existing job but altered in some form to result in lost time reduction, comprising the steps of:
   (a) creating a computer database by conducting an elemental analysis of a job's functions and requirements for an employer by breaking a job down into elemental tasks and the physical and mental requirements of each task; creating a parsable database of the jobs, workstation, tasks and elements to establish specific maximum physical requirements and required movements; and storing this elemental analysis on the computer database;
   (b) conducting an initial medical diagnosis of the injured worker by a physician examination of the worker and inputting the computer database with the initial injury report to determine the physical capabilities and limitations of the worker wherein the medical diagnosis comprises the steps of:
      a doctor seeing the injured worker patient;
      the doctor, inputting the data from the examination into the computer database based on the injury;
      the computer database automatically diagnosing the worker based on the inputted data;
      the computer database making recommendations regarding the worker's ability to handle certain tasks;
      the doctor reviewing the computer database recommendations and prescribing the computer database recommendations as maximum allowable restrictions on activities of the worker wherein the recommendations include specific maximum allowable physical and mental requirements and movements; and
      the physician's office inputting the maximum allowable restriction data into the computer database; and
   (c) using a risk assessment utility that is used to parse the computer database of past injuries to determine what elements of a job are more prone to causing injuries, wherein said risk assessment utility is used to also adapt a job or job elements to compensate or reduce the risks;
   (d) comparing by computer the elemental analysis and the medical diagnosis computer generated data to determine whether the worker can function in a new assignment of a particular job, wherein the particular job is either the current job, the different existing job, the current job but altered in some form, or the different existing job but altered in some form, by performing the step of:
      comparing the injured worker's inputted computer generated medical diagnosis of allowable physical and mental requirements and movements with each job's elemental analysis requirements to either:
      allow the injured worker to safely return to work by first determining if the injured worker's allowable capability exceeds each possible new assignment of elemental job requirements and then using the risk assessment utility to assess the risk for each job and altered job to assign a job for the injured worker that minimizes the risk of injury for the injured worker based on the computer database of past injuries; or
      prevent the injured worker from performing any job with tasks in the computer database exceeding the injured worker's allowable restrictions on activities.

2. The method as claimed in claim 1, wherein:
   (e) the computer database comprises information selected from the group consisting of the company's jobs, the company's workers, injuries to a company's workers, job candidates, required skills, required education, required certifications or credentials, governmental and legal requirements;
   (f) the computer database is searched by computer according to predetermined search criteria so as to result in a match between a worker and a job, between a diagnosis and a job, a possibility for adapting a worker or a job to fit the criteria, or to assess the risk inherent in a job; and
   (g) determining whether the worker can do the job.

3. A computer system executing the steps for determining whether an injured worker can return to work in their current job, a different existing job, the current job but altered in some form, or a different existing job but altered in some form, comprising:
   (a) creating a computer database for storing and comparing software utilities;
   (b) an elemental analysis utility for creating and using an integrated database of jobs, job functions, job tasks, and job requirements for an employer by breaking a job down into elemental tasks and the physical and mental requirements of each task;

creating a parsable database of the jobs, workstation, tasks and elements to establish specific maximum physical requirements and required movements; and storing this elemental analysis utility on the computer database;

(c) a medical diagnosis utility for creating and using an integrated database of worker injuries, and of injuries to a particular worker and storing the medical diagnosis utility and the integrated database of worker injuries on the computer database;

wherein a doctor seeing an injured worker, diagnoses the worker by inputting the injury into the medical diagnosing utility, wherein the medical diagnosis utility then makes recommendations regarding the worker's ability to handle certain tasks; wherein the doctor prescribes the computer generated recommendations as maximum allowable restrictions on activities of the worker including maximum allowable physical and mental requirements and movements;

(d) a risk assessment utility for parsing the computer database of past worker injuries to determine what elements of a job are more prone to causing injuries, wherein said risk assessment utility is used to also adapt a job or job elements to compensate or reduce the risks; and (e) a return to work utility to determine whether an injured or disabled worker can return to work in a new assignment of a particular job, wherein the particular job is either the current job, the different existing job, the current job but altered in some form or the different existing job but altered in some form, by performing the steps of:

comparing by computer the medical diagnosis of allowable physical and mental requirements and movements with each job's elemental analysis requirements to either:

allow the injured worker to safely return to work by first determining if the injured worker's allowable capability exceeds each possible new assignment of elemental job requirements and then using the risk assessment utility to assess the risk for each job and altered job to assign a job for the injured worker that minimizes the risk of injury for the injured worker based on the computer database of past injuries; or prevent the injured worker from performing any job with tasks in the computer database exceeding the injured worker's allowable restrictions on activities.

4. The computer system for executing the steps as claimed in claim 3, wherein:

(f) the computer database comprises information selected from the group consisting of the company's jobs, the company's workers, injuries to a company's workers, job candidates, required skills, required education, required certifications or credentials, governmental and legal requirements;

(g) the computer database is searched by the computer according to predetermined search criteria so as to result in a match between a worker and a job, between a diagnosis and a job, a possibility for adapting a worker or a job to fit the criteria, or to assess the risk inherent in a job; and (h) determining whether the worker can do the job.

\* \* \* \* \*